United States Patent [19]

Lodi

[11] Patent Number: 4,918,062

[45] Date of Patent: Apr. 17, 1990

[54] PHARMACEUTICAL COMPOSITIONS FOR THE TREATMENT OF CEREBRAL PSYCHO-ORGANIC SYNDROMES

[75] Inventor: Rosanna Lodi, Milan, Italy

[73] Assignee: Riace Establishment, Vaduz, Liechtenstein

[21] Appl. No.: 294,515

[22] PCT Filed: Apr. 2, 1988

[86] PCT No.: PCT/EP88/00276

§ 371 Date: Jan. 31, 1989

§ 102(e) Date: Jan. 31, 1989

[87] PCT Pub. No.: WO88/07860

PCT Pub. Date: Oct. 20, 1988

[30] Foreign Application Priority Data

Apr. 8, 1987 [IT] Italy .................. 20034 A/87

[51] Int. Cl.$^4$ ............................................. A61K 31/685
[52] U.S. Cl. ........................................ 514/76; 514/77; 514/78
[58] Field of Search ............................. 514/76, 77, 78

Primary Examiner—Stanley J. Friedman
Attorney, Agent, or Firm—Walter H. Schneider

[57] ABSTRACT

A pharmaceutical composition containing L-α-glycerylphosphorylcolamine as the principal active ingredient for use in the treatment of chronic cerebral psycho-organic syndromes of the involutive kind or due to cerebrovascular insufficiency.

1 Claim, No Drawings

PHARMACEUTICAL COMPOSITIONS FOR THE TREATMENT OF CEREBRAL PSYCHO-ORGANIC SYNDROMES

The invention refers to pharmaceutical compositions containing as the active principle L-α-glycerylphosphorylcolamine for the treatment of cerebral psycho-organic syndromes.

The L-α-glycerylphosphorylcolamine or L-α-glycerylphosphorylethanolamine (GPE) (J. Am. Chem. Soc. 75, 4510–14, 1953), physiological metabolite in the lipids metabolism, is a deacylated precursor of cephalins, particularly abundant phospholipids in the central nervous system.

The L-α-glycerylphosphorylcolamine is also a precursor of glycerylphosphorylcholine and of phosphatidylcholine.

According to what is presently known on the cerebral metabolism and biochemistry it is however impossible to devise any therapeutic use for GPE.

It has now been surprisingly found that GPE, administered to laboratory animals is able to significantly improve the response to the learning and memory tests, whereas, when administered to man, it has shown the ability to influence in a likewise significant way the neurophysiological parameters, the psychometric tests and the used neurologic scales.

Said pharmacological actions are probably due on one side to the activation of the phospholipids biosynthesis in the microsomes of the Central Nervous System (CNS) and on the other to the stimulation of the biosynthesis of the neurotransmitter acetylcholine, through the metabolic intermediates glycerylphosphorylcholine and phosphatidylcholine.

It is well known in fact that the frequent memory disturbances constantly found in aging are related with a decrease of the central cholinergic transmission: it has been shown in fact that a functional and anatomic impairment of cholinergic circuits constantly accompanies the alteration of the mnemonic functions (Drachman D. A., Sahakiam B. J.: Effects of cholinergic agents on human learning and memory, in: Nutrition and brain, 5, Barbeau A. et al. J. eds. 351–361, Raven Press Pubs, New York, 1979).

The validity of the invention is not in any way connected to the verification of the above stated mechanisms of action. The results obtained with GPE in pharmacological and clinical tests are reported hereinafter.

TOXICITY

It is meaningless to speak of subacute or chronic toxicity for GPE, which is physiological metabolite normally present in the human body.

As far as acute toxicity is concerned, the following data are obtained:

Oral route up to 3 g/kg did not cause either death or any symptomatology both in mice and rats and in rabbits.

Intramuscular route $LD_{50}$-in mice and rats $> 1500$ mg/kg in rabbits $> 1000$ mg/kg.

PHARMACOLOGICAL TESTS

The GPE administered i.p. to 20 male mice at the dose of 100 mg/kg subjected to the electroshock test as described by Esseman in Pharmacol. Res. comm. 5, 295–302, 1973, and at the same dose and for the same route to 20 male rats subjected to the pole-climbing test as described by Cook and Weindley (Ann. N.Y. Acad. Sci. 66, 740–752, 1957) has significantly shown the ability to activate learning and memory in comparison to the untreated animals.

CLINICAL TESTS

The above described pharmacological activity has been confirmed in clinical tests in the treatment of senile cerebral alteration, of both involutive and cerebro-vascular insufficiency origin, and of the related symptomatology, such as slowing of psychic activity, memory and alertness decrease, mood alteration, emotional weakness, irascibility, anxiety, etc.

20 patients (10 male and 10 female) 59 to 76 years old were treated; the overall clinical evaluation, taking into account the improvement of the neurophysiological and neurological exams carried out, of the psychometric tests and of the used neurological scale (De Renzi E., Nichelli P.: Verbal and non-verbal short-term memory impairment following hemispheric damage, Cortex, 11, 341–354, 1975; Bisiach E. et. al.: Neurologia Clinica, Ricerche di psicologia, Ed. F. Angeli, Milano, 1977; Cafarra P. et al.: Neuropsychological testing during a transient global amnesia episode and its follow-up, Acta Neurol. Scand. 63, 44–50, 1981; Kobs S. C.: Intelligence measurement, Mc Milan Pubs, New York, 1923), has shown a significantly positive therapeutic effect in 19 cases, whilst only one treatment was considered to be insufficient. The tolerability was always excellent.

The results are reported in the table.

| CASES | AGE | SEX | DIAGNOSIS | EVALUATION Activity | Tolerability |
|---|---|---|---|---|---|
| 1 | 73 | F | Cerebral vasculopathy with mental decline. | good | very good |
| 2 | 70 | M | Mental decline in cerebral vasculopathic. | insufficient | " |
| 3 | 73 | F | Cerebral vasculopathy with mental decline. | very good | " |
| 4 | 73 | F | Mental involution with serious cerebral atrophy. | very good | " |
| 5 | 69 | M | Alzheimer disease. | moderate | " |
| 6 | 63 | M | Cerebral atrophy with extrapiramidal syndrome and mental decline. | moderate | " |
| 7 | 68 | M | Front right circulatory cerebral insufficiency and mental decay. | good | " |
| 8 | 65 | F | Multifocal dementia. | good | " |
| 9 | 63 | F | Presenile Alzheimer disease. | good | " |
| 10 | 63 | M | Multifocal dementia with incipient cerebral atrophy. | very good | " |
| 11 | 71 | M | Cerebral vasculopathy with mental decline. | very good | " |
| 12 | 71 | F | Alzheimer disease with cerebral atrophy. | good | " |
| 13 | 76 | M | Cerebral vasculopathy with mental decline. | good | " |
| 14 | 59 | F | Vasculopathy prevailing in the vertebro-basilar circuit. | moderate | " |
| 15 | 75 | F | Cerebral vasculopathy with mental decline. | moderate | " |
| 16 | 70 | F | Alzheimer disease. | good | " |

-continued

| CASES | AGE | SEX | DIAGNOSIS | EVALUATION | |
|---|---|---|---|---|---|
| | | | | Activity | Tolerability |
| 17 | 71 | F | Alzheimer disease with initial cerebral atrophy. | very good | " |
| 18 | 65 | M | Alzheimer disease. | very good | " |
| 19 | 66 | M | Cerebral vasculopathy with cerebral atrophy. | good | " |
| 20 | 70 | M | Multifocal dementia. | good | " |

From what reported above, it is evident how GPE can be conveniently used in the therapy of chronic cerebral psycho-organic syndromes both of involutive kind and caused by cerebrovascular insufficiency and in the treatment of the symptomatology related therewith (poor attention and concentration ability, mental confusion, loss of memory, anxiety, emotional weakness, depressed mood, alteration of alertness condition).

For the considered therapeutic uses, GPE may be administered as such or in form of suitable pharmaceutical composition, using conventional techniques and excipients such as those described in "Remington's Pharmaceutical Sciences Handbook", Hack Pub. Co. New York, USA.

The preferred administration routes are the oral route and the parenteral route.

Examples of suitable pharmaceutical compositions comprise therefore capsules, tablets, solutions, syrups, sachets, vials.

The daily posology will depend on several factors such as the seriousness of the disease to be treated, patient's weight, age and sex, response to the treatment etc. It will generally range from 0,5 to 3 g daily, optionally divided in more administrations. Higher doses are not however contraindicated.

The following examples illustrate and do not limit the invention.

EXAMPLE 1

| Tablets | mg 250 | mg 500 |
|---|---|---|
| GPE | mg 250 | mg 500 |
| Lactose | mg 100 | mg 200 |
| Starch | mg 75 | mg 150 |
| Talc | mg 20 | mg 40 |
| Microcrys. cellulose | mg 50 | mg 100 |
| Magnesium stearate | mg 2 | mg 4 |

EXAMPLE 2

| Buvable vials | |
|---|---|
| GPE | mg 1.000 |
| Sodium saccharinate | mg 15 |
| Glycerol | mg 100 |
| Flavour | mg 20 |
| Purified water q.b. to | mg 10 |

EXAMPLE 3

| Lyophylized vials | mg 250 | mg 1.000 |
|---|---|---|
| GPE | mg 250 | mg 1.000 |

I claim:

1. A method of treating a patient suffering from chronic cerebral psycho-organic syndromes of the involute kind or due to cerebrovascular insufficiency which comprises administering to said patient a pharmaceutical composition containing as the principal active ingredient an effective amount of L-α-glycerylphosphorylcolamine in admixture with a pharmaceutically acceptable carrier.

* * * * *